US010165938B2

(12) United States Patent
Selcho et al.

(10) Patent No.: US 10,165,938 B2
(45) Date of Patent: *Jan. 1, 2019

(54) CONFIGURABLE MEDICAL VIDEO SAFETY SYSTEM (71) Applicant: Karl Storz Imaging, Inc., Goleta, CA (US)

(72) Inventors: Michael Selcho, Salt Lake City, UT (US); Hans-Uwe Hilzinger, Tuttlingen (DE); Devon Bream, Manhattan Beach, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 172 days.

This patent is subject to a terminal disclaimer.

(21) Appl. No.: 14/932,621

(22) Filed: Nov. 4, 2015

(65) Prior Publication Data
US 2016/0058277 A1 Mar. 3, 2016

Related U.S. Application Data (63) Continuation-in-part of application No. 13/675,825, filed on Nov. 13, 2012.

(51) Int. Cl.
*A61B 1/267* (2006.01)
*G06F 3/16* (2006.01)
(Continued)

(52) U.S. Cl.
CPC ............ *A61B 1/267* (2013.01); *A61B 1/0005* (2013.01); *G06F 3/017* (2013.01); *G06F 3/0346* (2013.01);
(Continued)

(58) Field of Classification Search
CPC ...... G06F 3/04817; G06F 3/147; G06F 3/167; A61B 2017/00017; A61B 2017/00199; A61B 2017/00203; A61B 2017/00207; A61B 2017/00225; A61B 2017/00367; A61B 1/267; A61B 1/00045; A61B 1/04; A61B 1/00112; A61B 1/00039; A61B 17/00
See application file for complete search history.

(56) References Cited

U.S. PATENT DOCUMENTS 5,788,688 A 8/1998 Bauer et al.
5,827,178 A 10/1998 Berall
(Continued)

OTHER PUBLICATIONS

OR 1 (R) Essential Drawings Drawn by: SS Dated: Sep. 9, 2008 13 pages.
(Continued)

*Primary Examiner* — Jacqueline Johanas
*Assistant Examiner* — Tessa Matthews
(74) *Attorney, Agent, or Firm* — Whitmyer IP Group LLC (57) ABSTRACT A medical image routing system that allows for a user to override the current routing of medical image data such that a user need only activate an interface to automatically interrupt the the first medical image data routing to a display(s) with the second medical image data automatically routed to the display(s). Upon activation of the interface a second time, the first medical image data routing is automatically reestablished and the second medical image data is automatically interrupted.

24 Claims, 8 Drawing Sheets (51) Int. Cl.

| | | |
|---|---|---|
| *G06F 3/147* | (2006.01) | |
| *G06F 3/0481* | (2013.01) | |
| *G06F 3/01* | (2006.01) | |
| *G06F 3/041* | (2006.01) | |
| *A61B 1/00* | (2006.01) | |
| *G06F 19/00* | (2018.01) | |
| *G06F 3/0346* | (2013.01) | |

(52) U.S. Cl.
CPC .......... *G06F 3/041* (2013.01); *G06F 3/04817* (2013.01); *G06F 3/147* (2013.01); *G06F 3/167* (2013.01); *G06F 19/00* (2013.01); *G06F 19/321* (2013.01)

(56) References Cited

U.S. PATENT DOCUMENTS

| | | | |
|---|---|---|---|
| 6,543,447 B2 | 4/2003 | Pacey | |
| 6,655,377 B2 | 12/2003 | Pacey | |
| 6,890,298 B2 | 5/2005 | Berci et al. | |
| 7,044,909 B2 | 5/2006 | Berci et al. | |
| 8,029,440 B2 | 10/2011 | Birnkrant et al. | |
| 8,069,420 B2 | 11/2011 | Plummer | |
| 8,627,219 B2 * | 1/2014 | Wang | G06F 1/181 715/762 |
| 9,119,700 B2 * | 9/2015 | Boukhny | A61F 9/00745 |
| 9,283,347 B2 * | 3/2016 | Heesch | A61M 16/104 |
| 2003/0171740 A1 | 9/2003 | Stiller et al. | |
| 2004/0024384 A1 | 2/2004 | Novak | |
| 2006/0152516 A1 * | 7/2006 | Plummer | G06F 19/321 345/538 |
| 2008/0249370 A1 | 10/2008 | Birnkrant et al. | |
| 2011/0088694 A1 | 4/2011 | Tobia et al. | |
| 2012/0278759 A1 * | 11/2012 | Curl | G06F 19/327 715/804 |
| 2014/0135648 A1 * | 5/2014 | Holoien | A61B 1/0005 600/562 |
| 2016/0000299 A1 * | 1/2016 | Itai | A61B 6/5223 600/103 |
| 2016/0000517 A1 * | 1/2016 | Kehat | A61B 1/2676 600/424 |
| 2016/0037998 A1 * | 2/2016 | Kawashima | A61B 1/00006 600/102 |

OTHER PUBLICATIONS

OR1(R) Essential—Instruction Manual; (c) 2009 Karl Storz Endoscopy—America, Inc.; 36 pages.

* cited by examiner

FIGURE 7

CONFIGURABLE MEDICAL VIDEO SAFETY SYSTEM

FIELD OF THE INVENTION

The system relates to an image routing system, and more particularly to a medical image routing system utilized in an operating room providing prioritized image routing.

BACKGROUND OF THE INVENTION

A wide variety of operating room systems are known for performing both diagnostic and surgical procedures. In particular, systems have been provided that allow a surgeon to perform a procedure with a variety of medical and operating room equipment. This equipment ranges from visual imaging tools (e.g., endoscopes, cameras, digital x-ray, ultrasound, computer tomography, magnetic resonance imaging, etc.) and systems, to medical devices (e.g. tools for cutting, grasping, extracting, irrigating, etc.), and other operating room equipment.

In particular systems, operating room visualization equipment has been provided that allows for visualization of the interior of an organ or joint while a surgeon is conducting a procedure. These visualization systems allow for a surgeon to view, typically on a surgical monitor placed either in or adjacent to, the sterile environment, a location inside the body where the procedure is being performed. These systems have further allowed for the recording of still pictures and video recordings of the area and procedure. Not only have the surgeon and those in the operating room been able to view the surgical site on the surgical monitor, but systems have further provided for the transfer of visualization information via a network connection to remote locations from the operating room. These systems have further allowed for previously generated diagnostic surgical image data to be retrieved and displayed as required during a surgical procedure. In this manner, individuals have had the capacity to view a surgical procedure from different locations. This has proved to be a very helpful educational tool (e.g. medical students can view a medical procedure from a class room) and has allowed for specialists to view the surgical procedure from a distance to provide expert analysis and input to the surgeon.

A number of medical procedures require the patient be maintained under anesthesia, typically by means of IV administered anesthetic or a gas mixture administered to the patient, or both. In such cases, a ventilator is provided which helps a patient breathe by giving oxygen to the patient through an endotracheal tube inserted into the trachea. It should be noted that when the tube is first inserted into the patient, the patient is asleep and is hyperoxygenated. Upon giving the patient anesthesia, the patient is quickly paralyzed and is not breathing on their own. It is critical for a physician to work quickly to insert the endotracheal tube into the patient, so as to ventilate the patient.

The insertion of the endotracheal tube involves risks that a physician and/or anesthesiologist seeks to avoid or at least minimize. It is estimated that between one in 6,000 to one in 8,000 general anesthesia procedures result in death. There are of course many causes but of these it is estimated that about one third of them are caused by the intubation procedure.

Some obstacles encountered by the anesthesiologist upon insertion of the endotracheal tube include the remoteness of the location where the tube is to be positioned, the consequent restriction of view as the tube is inserted, variations and anomalies in the anatomy of the patients, an uncomfortable and unnatural position for the anesthesiologist while holding the instrument, the potential need to change blades during the procedure, and the necessity for rapid intubation.

With the advent of endoscopic equipment and small cameras, instrumentation can enable viewing of a patient's cords and larynx on a video screen facilitating the intubation of the patient in a relatively quick and safe manner. A number of video laryngoscopes have been known including U.S. Pat. Nos. 5,827,178; 6,655,377; 6,543,447; 6,890,298; 7,044,909 and 8,029,440. Typically, these video laryngoscopes route video feeds to dedicated video monitors located adjacent to the laryngoscope (e.g. a video screen mounted beside or right on the handle of the laryngoscope).

As operating room control systems develop, the use of video displays and control systems continues to expand. U.S. Pat. No. 8,069,420 to Roderick Plummer (the Plummer patent) discloses an operating room system that allows for videos to be displayed on screens in the operating room. In particular, the Plummer patent allows for routing of video image data to a selected destination.

While steps have been made in the presentation of endoscope video imaging in an operating room system, the integration of video laryngoscopes into the operating room control system has not been effectively addressed. In current systems, the intubation process typically occurs with a system separate and apart from the operating room system. However, if during a surgical procedure it becomes necessary to re-intubate the patient, time is critical. Requiring moving the operating room equipment aside, moving the laryngoscope equipment in its place, intubating the patient, moving the laryngoscope equipment aside and moving the operating room equipment back into place can often lead to delayed time to intubate the patient and increased time under anesthesia, both of which are highly undesirable.

Likewise, the necessity of having to program the routing of the image data that is generated by the laryngoscope wastes valuable time that the patient is disconnected from the ventilation machine and not breathing. It also disadvantageously extends the time the patient is maintained under general anesthesia.

SUMMARY OF THE INVENTION

Accordingly, it is an object of the present invention to provide an operating room system that allows an anesthesiologist to quickly and efficiently intubate a patient by use of a video laryngoscope. The video laryngoscope provides a video feed to a display positioned in the operating room in a manner that allows an anesthesiologist to easily see the video display so as to intubate the patient.

It is also desired to provide an operating room system that allows an anesthesiologist to quickly and efficiently interrupt a video feed to an operating room system display such that the display temporarily provides a video laryngoscope video feed to aid an anesthesiologist to intubate the patient.

It is a further object of the invention to provide an anesthesiologist with the ability to route video laryngoscope data to a display positioned in the operating room with a single selection.

It is another object of the invention to provide an operating room system that integrates both a video laryngoscope and a video endoscope into a single centralized operating room system.

These and other objects are achieved by an operating room control system that includes a computer, an interface that includes input connections for an imaging device generating surgical image data, at least one display for displaying the surgical image data, and a video laryngoscope, where the video laryngoscope generates laryngoscope image data that is provided to the interface.

In certain embodiments, the system is provided such that upon activation of the interface, which may comprise a touchscreen interface positioned in the sterile surgical environment adjacent to the surgeon, the routing of surgical image data to the display is interrupted and laryngoscope image data is instead shown on the display. This routing of laryngoscope image data can be accomplished by a single selection by the anesthesiologist (e.g., tapping of an icon on the touchscreen that selects the laryngoscope as the interface).

In certain embodiments, upon activation of the interface for a second time (again by a single selection of an icon on the touchscreen), the routing of laryngoscope image data to the display is interrupted and surgical image data is instead shown on the display.

In certain embodiments, a video laryngoscope may be integrated into a centralized operating room control system, such that the video laryngoscope may utilize the same display(s) utilized by a surgeon during a medical procedure. Thus no separate laryngoscope display and associated equipment need be positioned in the operating room. Rather, the anesthesiologist can use the surgical display(s) already located in the operating room. However, the challenge is how to quickly and easily switch between multiple different imaging sources (endoscope and laryngoscope).

Under normal surgical conditions, this would not normally be a problem because the patient is intubated prior to any surgical procedure occurring. The anesthesiologist has the time to insert the endotracheal tube into the patient's trachea while viewing the patient's throat/airway on the surgical monitor. Once the endotracheal tube is put in place, the laryngoscope is removed and the endotracheal tube is connected to a ventilator. At this point, the anesthesiologist will monitor the patient's vital signs and the administration of anesthesia. The surgeon may then use the various displays to view surgical image data and perform the surgical procedure as needed.

However, in the event that it is determined that a patient needs to be re-intubated, it is critical that the intubation process happen quickly as the patient is not breathing. The challenge occurs if the display used by the anesthesiologist for intubation is displaying surgical image data. This becomes even more challenging for systems that allow for complex routing of video information, for example, saving of the surgical image data to one or more storage devices, and/or displaying the surgical video data on multiple displays in the operating room (e.g., the main surgical monitor and various additional surgical monitors).

Accordingly, an interface is provided that allows the anesthesiologist to override the routing of the surgical image data to the surgical monitor and automatically route the laryngoscope image data to a display for the anesthesiologist to utilize for the intubation process. This allows the anesthesiologist to immediately take control of a display to re-intubate the patient and re-connect the endotracheal tube to the ventilator. It is further understood that from the same location the anesthesiologist can reconstitute the routing of the surgical image to the display, as well as to the configured storage devices by activation of the interface. This effectively allows the anesthesiologist to instantly commandeer the display system (or at least one of the displays) for intubation purposes and then return the display back to displaying surgical image data without the need for any reprogramming, thereby reducing the time the patient is under anesthesia and minimizing the intubation time.

In certain embodiments, the interface comprises any type of device that allows for interruption of the surgical image data and automatic connection of the laryngoscope image data and vice versa when the anesthesiologist has finished the intubation process.

In certain embodiments, the interface comprises an icon located on a touchscreen accessible by the anesthesiologist. However, it should be noted that virtually any type of interface could be used including, for example, an emergency intubation button may be positioned in the vicinity of the anesthesiologist.

In certain embodiments, upon activation of the interface, the laryngoscope image data may automatically be displayed on the main surgical monitor, on a secondary display, on the touchscreen provided for the anesthesiologist or any combination thereof.

In the certain embodiments, additional medical information may be displayed on the touchscreen for the anesthesiologist including, for example, patient vital signs, anesthesia levels being administered, settings of the ventilation, and the like. The system may be programmed so that the laryngoscope image data is presented on the display desired. In the event the anesthesiologist desires the laryngoscope image data be displayed on the touchscreen, it is contemplated that the laryngoscope image data can immediately be displayed in a screen over top of the medical data being displayed on the touchscreen to provide a large image for the anesthesiologist. It should be understood that this is only a few embodiments and arrangements for the emergency display of laryngoscope image data and those of skill in the art may come up with many ways of automatically routing the laryngoscope image data without deviating from the invention.

For this application the following terms and definitions shall apply:

The term "network" as used herein includes both networks and internetworks of all kinds, including the Internet, and is not limited to any particular network or inter-network.

The terms "coupled", "coupled to", "coupled with", "connected", "connected to", and "connected with" as used herein each mean a relationship between or among two or more devices, apparatus, files, programs, media, components, networks, systems, subsystems, and/or means, constituting any one or more of (a) a connection, whether direct or through one or more other devices, apparatus, files, programs, media, components, networks, systems, subsystems, or means, (b) a communications relationship, whether direct or through one or more other devices, apparatus, files, programs, media, components, networks, systems, subsystems, or means, and/or (c) a functional relationship in which the operation of any one or more devices, apparatus, files, programs, media, components, networks, systems, subsystems, or means depends, in whole or in part, on the operation of any one or more others thereof.

The term "surgical image data" as used herein is intended to distinguish visual data generated before or during a surgery from "laryngoscope image data" which is generated during patient intubation. Surgical image data may be defined as any visual data related to and for the facilitation of a surgery, excluding visual data generated during patient intubation. Surgical image data may be for example, endoscopic images, digital x-ray images, ultrasound images, computer tomography images, magnetic resonance imaging, and the like; while laryngoscope image data is generated only during patient intubation.

In one embodiment of the present invention an operating room control system is provided comprising a computer having a network connection, and a storage accessible by the computer. The system also includes a controller coupled to the computer that provides for connection to an imaging device generating surgical image data, an interface, and a video laryngoscope, where the video laryngoscope generates laryngoscope image data. The system further includes a display coupled to the controller and surgical image data is routed to and shown on the display when an imaging device is connected to the system. The system is provided such that upon activation of the interface, routing of the surgical image data to the display is interrupted and laryngoscope image data is routed to the display when a video laryngoscope is connected to the system.

In certain embodiments, said display comprises at least two displays, wherein the single selection of the interface automatically routes the laryngoscope image data to at least one of said at least two displays.

In certain embodiments, the laryngoscope image data shown on said display is automatically routed to and saved on said storage.

In certain embodiments, upon a single selection of the interface a second time, routing of the laryngoscope image data to said display is interrupted and routing of surgical image data to said display is reestablished.

In certain embodiments, routing of surgical image data to said display further includes routing of surgical image data to said storage, and upon reestablishment of the routing of surgical image data to said display, routing of surgical image data to said storage is also reestablished.

In certain embodiments, the system further comprises a touchscreen coupled to said controller and the single selection of the interface comprises an icon on said touchscreen.

In certain embodiments, the system further comprises a voice control system coupled to said controller and the single selection of the interface comprises a voice command detected by the voice control system.

In certain embodiments, the system further comprises a gesture recognition control system coupled to said controller and the single selection of the interface comprises a gesture recognized by the gesture recognition control system.

In certain embodiments, upon the single selection of said interface, the laryngoscope image data is automatically displayed on said touchscreen.

In certain embodiments, the system further comprises at least one medical tool coupled to said controller, wherein upon the single selection of the interface, the functioning of said at least one medical tool is automatically changed.

In certain embodiments, the function change of said at least one medical tool is to set the medical tool to a predetermined setting.

In certain embodiments, said at least one medical tool is selected from the group consisting of: catheterization devices, bi-polar cutting devices, lasers, rotating cutting devices, cell collection devices, suction devices and combinations thereof.

In certain embodiments, the system further comprises at least one piece of medical equipment coupled to said controller, wherein upon the single selection of the interface, the functioning of said at least one piece of medical equipment is automatically changed.

In certain embodiments, the function change of said at least one piece of medical equipment is to set the at least one piece of medical equipment to a predetermined setting.

In certain embodiments, said at least one piece of medical equipment is selected from the group consisting of: insufflation equipment, irrigation equipment, vacuum equipment, respiratory equipment and combinations thereof.

In another embodiment of the present invention an operating room control system is provided comprising a computer having a network connection, a storage device accessible by the computer, and a controller coupled to the computer. The system also includes an imaging device coupled to the controller and generating surgical image data and an interface coupled to the controller. The system further includes a video laryngoscope coupled to the controller and generating laryngoscope image data, and a display coupled to the controller and surgical image data is routed to and shown on the display. The system is provided such that upon activation of the interface, routing of the surgical image data to the display is interrupted and laryngoscope image data is automatically routed to the display. The system is further provided such that upon activation of the interface a second time, routing of the laryngoscope image data to said display is interrupted and routing of surgical image data is automatically routed to the display.

In still another embodiment of the present invention an operating room control system is provided comprising a computer having a network connection, a storage accessible by the computer, and a controller coupled to the computer. The controller provides for connection to an imaging device generating image data, an interface, and a video laryngoscope, where the video laryngoscope generates laryngoscope image data. The system further comprises a display coupled to the controller where image data is routed to and presented on the display based at least in part on programmed settings. The system is provided such that upon a single selection of the interface, routing of the surgical image data to the display is interrupted and laryngoscope image data is automatically routed to the display based at least in part on the programmed settings.

In a further embodiment of the present invention an operating room control system is provided comprising a computer having a network connection and a storage accessible by the computer. The system further comprises a controller coupled to the computer and a touch screen having an interface. The touch screen that provides for connection to an imaging device generating image data, a video laryngoscope, where the video laryngoscope generates laryngoscope image data, and at least one medical tool. The system further comprises at least two displays coupled to the controller where image data is routed to and presented on the display based at least in part on programmed settings. The system is provided such that upon a single selection of the interface, routing of the surgical image data to the display is interrupted and laryngoscope image data is automatically routed to one of the at least two displays based at least in part on the programmed settings.

In certain embodiments, upon the single selection of the interface, routing of the surgical image data to said display is interrupted and laryngoscope image data is automatically routed to both of said at least two displays.

In certain embodiments, the laryngoscope image data shown on said one of said at least two displays is automatically routed to and saved on said storage.

In certain embodiments, said interface comprises an icon on said touchscreen.

In certain embodiments, said at least one medical tool is selected from the group consisting of: catheterization devices, bi-polar cutting devices, lasers, rotating cutting devices, cell collection devices, suction devices and combinations thereof.

In certain embodiments, upon the single selection of the interface, the functioning of said at least one medical tool is automatically changed.

In certain embodiments, the function change of said at least one medical tool is to set the medical tool to a predetermined setting.

In certain embodiments, the system further comprises at least one piece of medical equipment coupled to said controller, wherein upon the single selection of the interface, the functioning of said at least one piece of medical equipment is automatically changed.

In certain embodiments, the function change of said at least one piece of medical equipment is to set the at least one piece of medical equipment to a predetermined setting.

In certain embodiments, said at least one piece of medical equipment is selected from the group consisting of: insufflation equipment, irrigation equipment, vacuum equipment, respiratory equipment and combinations thereof.

Other objects of the invention and its particular features and advantages will become more apparent from consideration of the following drawings and accompanying detailed description.

DETAILED DESCRIPTION OF THE INVENTION

Referring now to the drawings, wherein like reference numerals designate corresponding structure throughout the views.

Figure 1:
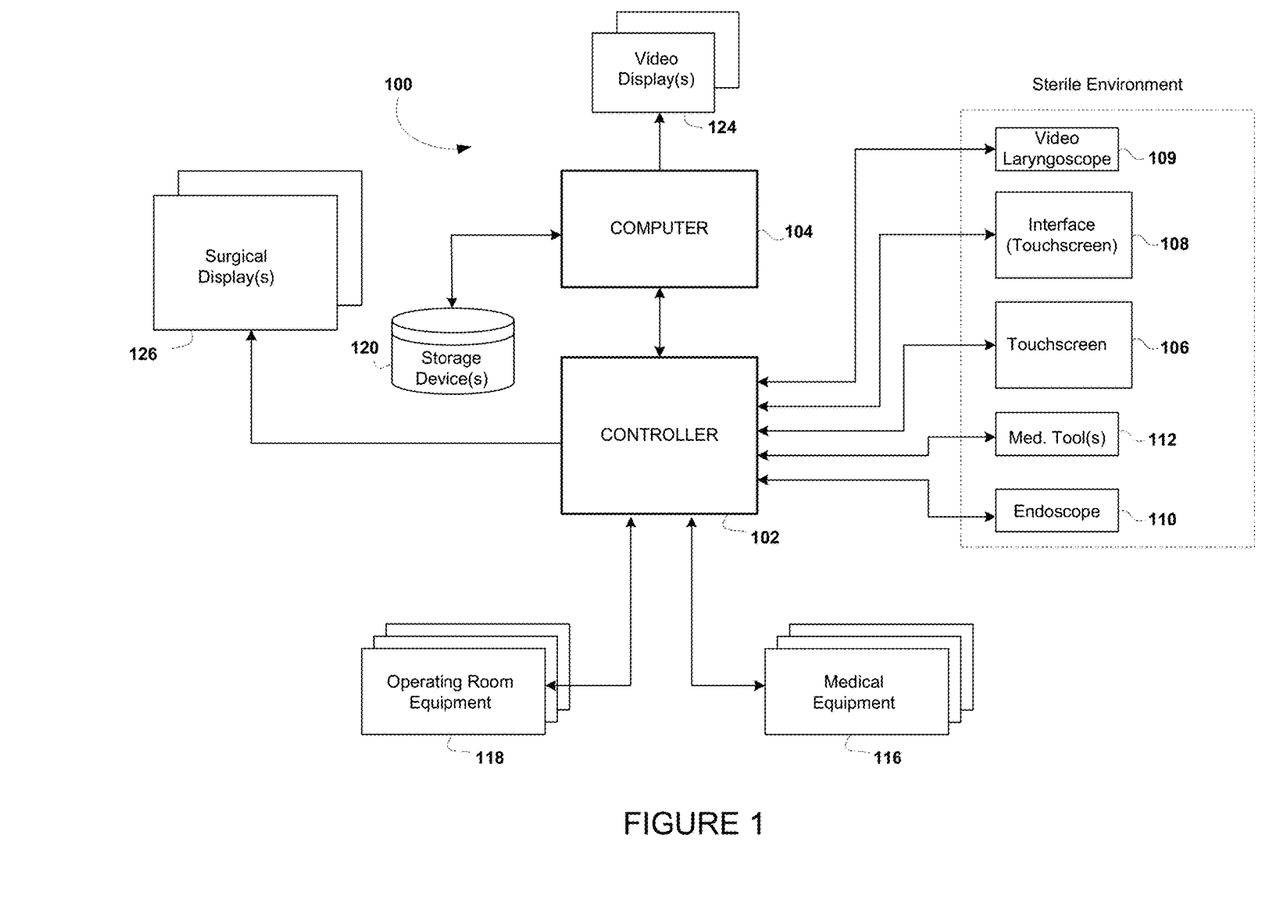
FIG. 1 is a block diagram of an advantageous embodiment of the present invention.

FIG. 1 is a block diagram of operating room control system 100 that generally includes a controller 102 connected to a computer 104. The controller 102 would typically be positioned or located in the operating room in proximity to the various equipment connected thereto and in one embodiment, would be rack-mounted. It is further understood that computer 104 may also be located in the operating room and rack-mounted, however, this is not required as the controller 102 could be coupled to computer 104 via, for example, a network connection.

Connected to controller 102 is touch screen 106, which provides an interface for a user to control and to interface with operating room control system 100. Touch screen 106 is shown positioned in the sterile environment and is accessible by a surgeon performing a procedure. The touch screen 106 may comprise virtually any type of commercially available touch screen device and would typically be mounted on a boom or arm allowing the user to position the touch screen 106 in a manner convenient for use (e.g., adjacent to or over the patient). Alternatively, the touch screen could be connected to, for example, a medical equipment rack.

An interface 108 (e.g., touch screen) is also illustrated positioned in or adjacent to the sterile environment and connected to controller 102. Interface 108 may be provided for an anesthesiologist to view the patient's vital signs and control the administration of anesthesia to the patient. It is understood that interface 108 may provide control of various medical equipment 116, and may have the ability to access, for example, the hospital information system to pull up the patient's records and information. Still further, the anesthesiologist may be provided with the ability to record or save the information presented on interface 108 as desired in a manner and to any storage device, such as storage device(s) 120. Interface 108 may comprise one or more pieces of equipment that allow for the control and administration of anesthesia as well as for monitoring the patient. The idea is to provide maximum flexibility to the system users to increase safety, efficiency and ease of use.

Also shown in FIG. 1 is video laryngoscope 109, which may comprise any commercially available laryngoscope that is capable of generating digital image data. As previously discussed, it is common to intubate a patient prior to a surgical procedure in order to place an endotracheal tube in the patient's trachea, which is in turn connected to a ventilator to provide oxygen and other medical/anesthetic gases to the patient during the surgical procedure. The video laryngoscope 109 generates laryngoscope image data, which is transmitted to the operating room system to be shown on the surgical display and/or the video monitor as desired. The laryngoscope image data provides the anesthesiologist a view of the inside of the patient's throat and trachea to aid the anesthesiologist in the intubation procedure. Once the endotracheal tube it properly inserted, the video laryngoscope 109 is withdrawn and the surgeon can utilize the surgical display(s) 126 and video display(s) 124 to display surgical image data during the surgical procedure. During the surgical procedure, surgical image data is routed to the display(s) based on the surgeon's preferences and is also routed to selected storage devices according to the surgeon's preferences. The interface 108 allows the anesthesiologist to quickly and efficiently route laryngoscope image data to a display(s) in the event that an emergency intubation procedure is required.

Accordingly, the interface 108 allows the anesthesiologist at a single location to override the routing of the surgical image data and automatically route the laryngoscope image data to surgical display(s) 126 and/or video display(s) 124. It is further understood that interface 108 also allows the anesthesiologist to reestablish the routing of the surgical image to surgical display(s) 126 and/or video display(s) 124, as well as to the configured storage devices. This effectively allows the anesthesiologist to instantly take control of the various displays for emergency intubation purposes and then turn the display system back over to the surgeon without the need for any reprogramming thereby reducing the time the patient is under anesthesia and minimizing any potential intubation time.

The interface 108 may comprise any type of device that allows for interruption of the surgical image data and automatic connection of the laryngoscope image data and vice versa when the anesthesiologist has finished the intubation process and, as illustrated in FIG. 1, may or may not be associated with a touch screen. For example, in one embodiment, the interface 108 comprises an interface in the form of an icon located on the touch screen and accessible by the anesthesiologist.

It is further contemplated that upon activation of the interface, the laryngoscope image data may automatically be displayed on the main surgical display(s), on a secondary display(s) (e.g., video display 124), on the touchscreen provided for the anesthesiologist or any combination thereof. The goal is to provide maximum flexibility for the anesthesiologist to be able to easily view the laryngoscope image data to intubate the patient and then quickly turn the display(s) back over to the surgeon for minimum interruption of the surgical procedure in the event the surgeon's display was overridden.

While an interface in the form of an icon positioned on the touch screen is envisioned as one embodiment of interface 108, virtually any type of interface could be used including, for example, an emergency intubation button placed in the vicinity of the anesthesiologist that will automatically route laryngoscope image data as previously discussed. It further contemplated that interface 108 may comprise a voice control system and/or a gesture recognition control system (not shown) by which the anesthesiologist and/or surgeon may select surgical image data and/or laryngoscope image data for display on a desired display or displays, and/or for storage. Such a voice control system and/or gesture recognition control system may include a sensor and/or a microphone that interprets voice and/or gesture from a user.

Also illustrated in FIG. 1 is endoscope 110 and medical tool(s) 112 connected to controller 102. Endoscope 110 may comprise virtually any type of video endoscope that allows for visualization of a surgical site inside of the body and may be flexible or rigid and have a detachable or integral camera. It is further contemplated that endoscope 110 may utilize a wired or wireless connection to controller 102 and have a CCD or CMOS imager (not shown) positioned on the endoscope for converting received light to a digital image stream.

Likewise, medical tool(s) 112 may comprise a wide variety of medical tools used by the surgeon including, but not limited to: catheterization devices, bi-polar cutting devices, lasers, rotating cutting devices, cell collection devices, suction devices and the like. It is understood that many of these medical tools 112 may be manufactured by different companies and therefore the command and control signals for each of the medical tools may differ. Controller 102 is provided to interface between the numerous differing types of signal formats such that the user may control a medical tool(s) from the touchscreen 106 if desired.

Medical equipment 116 is illustrated having a number of boxes to indicate that there may be a plurality of medical equipment 116 connected to controller 102. Typically medical equipment 116 is rack-mounted on a wheeled cart allowing for the equipment to be placed conveniently and in proximity to the sterile environment. Medical equipment 116 will vary depending on the procedure being performed, however, to provide some context to the types of equipment that medical equipment 116 may comprise, a non-exhaustive list is provided including: insufflation equipment, irrigation equipment, vacuum equipment, respiratory equipment and the like. It should be understood that a great number of different types of equipment may be used depending upon the procedure to be performed. As with medical tool(s) 112, it is contemplated that medical equipment 116 may be equipment manufactured by many different companies and therefore have command and control signals with diverse formats and requirements. Accordingly, controller 102 is provided to send and receive data to and from medical equipment 116 such that the medical equipment 116 may be controlled from touchscreen 106.

Also shown in FIG. 1 is operating room equipment 118 connected to controller 102. Like medical equipment 116, operating room equipment 118 is controllable from either touchscreen 106 or interface 108. Operating room equipment 118 may comprise a wide variety of equipment that may be desirable to control by the surgeon or nurse including, but not limited to, the operating room lights, the operating room blinds or shades, and the positioning of the operating room table.

Still further, storage device(s) 120 is shown connected to computer 104. Storage device(s) 120 may comprise virtually any type of digital storage device including, solid state hard drive devices, magnetic hard drives devices, optical drive devices, removable storage devices and the like. For example, it may be desired to record a part or all of the procedure from the video endoscope 110 to a DVD inserted into computer 104. However, it may further be desire to save a part or all of the procedure to a hard drive device in the hospital information system for the hospitals records. Still further, the surgeon may desire to save a part or all of the procedure directly to a storage device on the surgeon's computer in the surgeon's office.

Video display(s) 124 is illustrated connected to computer 104. It should be understood that operating room control system 100 allows for video feeds to remote locations for telesurgery and teleconferencing such that a surgeon at a remote location could view the surgical procedure and provide input or comments to the surgeon performing the procedure. In addition, a video feed could be provided to a classroom environment for educational purposes so that medical students have the opportunity to see a particular medical procedure from a remote location.

Surgical display(s) 126 is shown connected to controller 102 and may comprise one or more surgical monitors positioned in the operating room. Typically a main surgical monitor (typically a large (40"-60") flat panel display) is provided in the operating room and quite often, numerous surgical monitors are positioned at various locations in the operating room. It is contemplated that the video feed from the video endoscope 110 will be displayed on surgical display(s) 126. While surgical display(s) 126 are shown connected to controller 102, it is understood that they may alternatively, be directly connected to computer 104.

Figure 2A:
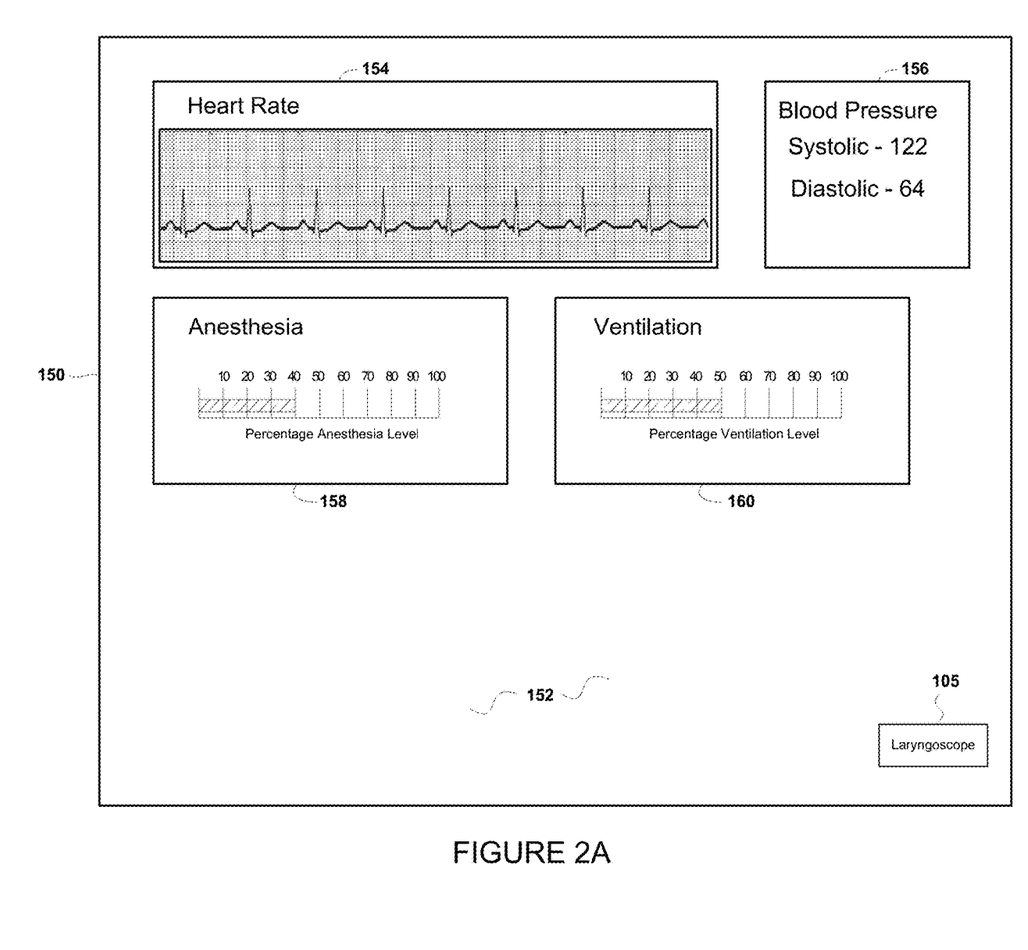
FIG. 2A is an illustration of an embodiment of the present invention according to FIG. 1.

Turning now to FIG. 2A, an illustration of one embodiment of the present invention is provided in which various interfaces are provided on the front panel 152 of a touchscreen 150 having an interface 105 positioned thereon in the form of an icon.

The layout and type of medical information presented on the touchscreen 150 is merely presented to be typical of some information that may advantageously be presented to the anesthesiologist and is not intended to comprise a comprehensive list. It will be understood by those of skill in the art that numerous and varied medical information may be presented on the touchscreen depending upon the type of medical procedure being performed. In this particular example, a heart rate interface 154, a blood pressure interface 156, an anesthesia interface 158 and a ventilation interface 160 are all presented.

In the event that the anesthesiologist determines that the patient needs to be intubated (or re-intubated), the anesthesiologist need only touch the interface (emergency intubate icon) 105 located on the touchscreen 150.

Figure 3:
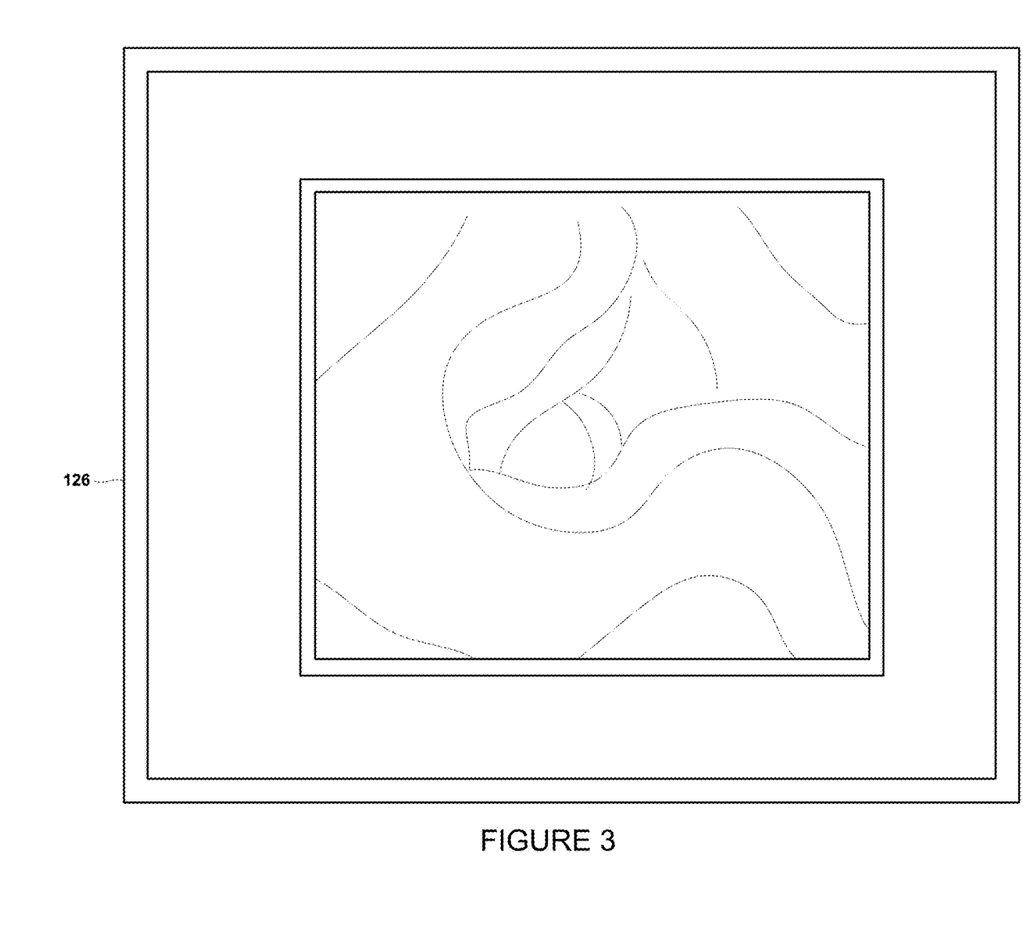
FIG. 3 is an illustration of a monitor according to an embodiment of the present invention of FIG. 1.
Figure 4:
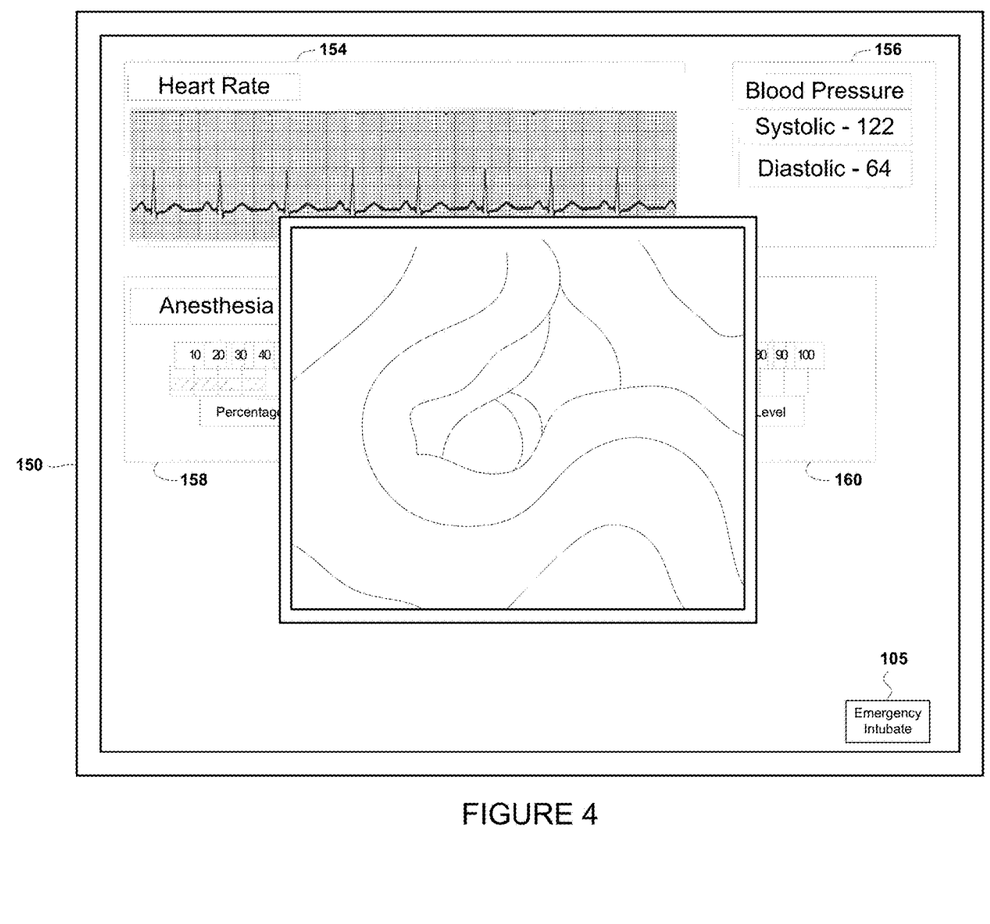
FIG. 4 is an illustration of a monitor according to an embodiment of the present invention of FIGS. 2A and 2B.

FIGS. 3 and 4 illustrate several embodiments of how the laryngoscope image data may be presented to the anesthesiologist. For example, FIG. 3 shows the laryngoscope image data automatically shown on surgical display(s) 126 and may further be shown on video display(s) 124 as desired. The laryngoscope image data may take up a portion of or the entire the surgical display(s) 126. Likewise, while no surgical image data is illustrated as being shown on the surgical display(s) 126, it is understood that the laryngoscope image data may simply be overlain (e.g., in a window) on the surgical image data, or the surgical image data could be shut off during routing by the anesthesiologist. Any configuration that allows the anesthesiologist to immediately view the laryngoscope image data is possible.

Still another embodiment in FIG. 4 shows the laryngoscope image data presented on the touch screen 150, which is positioned adjacent to the anesthesiologist. This may be particularly desirable as the touch screen can be mounted on a boom or arm and be fully adjustable allowing the anesthesiologist to quickly and easily adjust the touch screen for intubation. Alternatively, the laryngoscope image data may be presented on one of a plurality of displays in the operating room so as not to interrupt the surgeon's view of the surgical site, but still allowing the anesthesiologist to intubate the patient.

Once the anesthesiologist has completed the intubation procedure, touching the interface (emergency intubate icon) 105 a second time can work to interrupt the routing of laryngoscope image data to the display(s) and reestablish the routing of surgical image data to the display(s). It should also be noted that the routing of surgical image data to selected storage devices may also be reestablished as well as the settings of various medical devices and equipment. For example, it may be advantageous to automatically adjust the settings of select medical tools and equipment to a predetermined setting (e.g., to a low setting or even off) in the event the interface 108 is activated.

This allows for a single selection (e.g., selection of a new interface) to route the laryngoscope image data to a previously selected display(s) and for a single selection a second time to reestablish all of the image routing and tool/equipment settings automatically without any need to reprogram the system. It should be noted that the destination for the video laryngoscope data is not selected during this routing process as only the input is selected (e.g., the laryngoscope) while the previously programmed output (the display(s) previously presenting the surgical image data) continues to be utilized. In other words, the anesthesiologist need only select the new interface which image data will automatically be routed to the previously programmed output location.

Figure 2B:
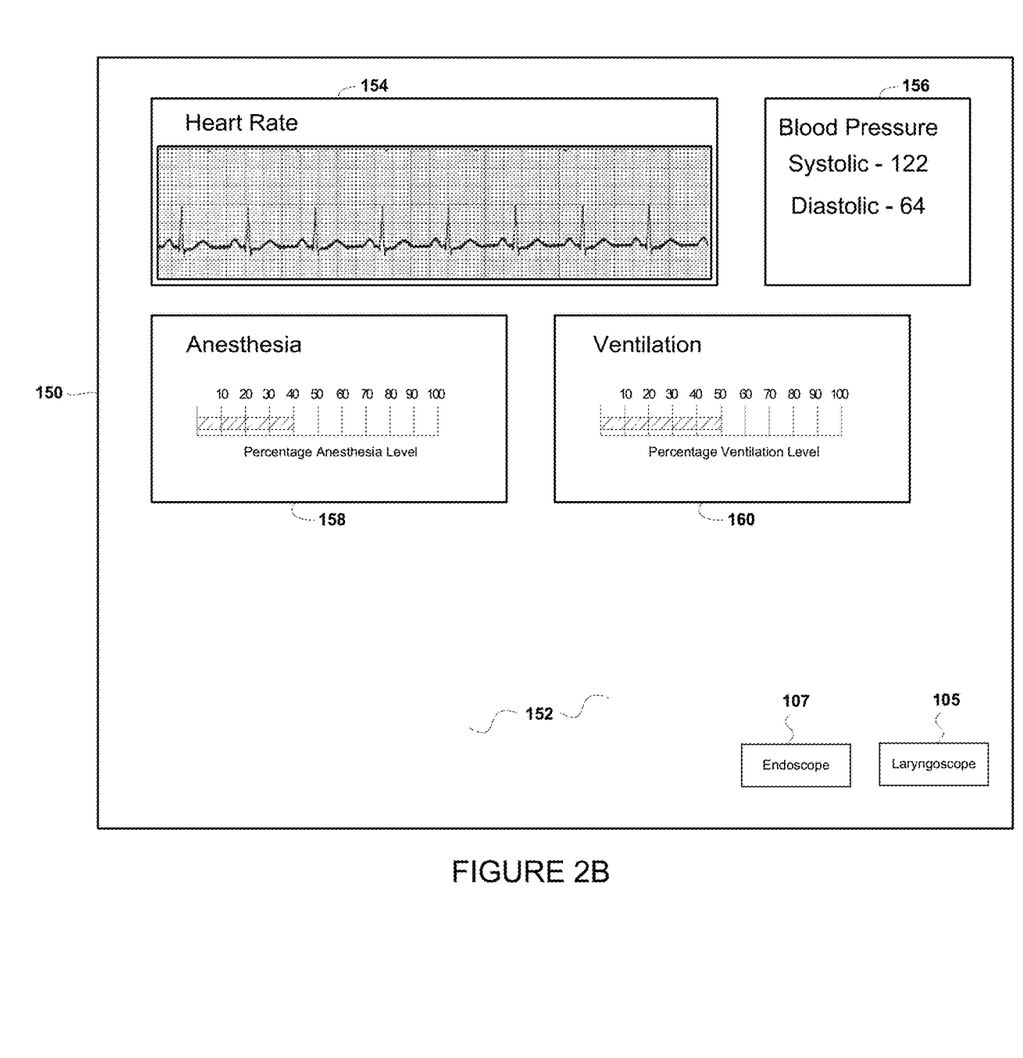
FIG. 2B is an illustration of an embodiment of the present invention according to FIG. 1.

While a single interface 105 is shown on the touchscreen 150, it is contemplated that multiple icons could be displayed on touchscreen 150, each icon representative of a video input device. For example, an endoscope icon could be positioned adjacent to the laryngoscope icon such that the anesthesiologist could select the laryngoscope icon to route the laryngoscope image data as previously discussed. Then, when finished with the intubation, the anesthesiologist could select the endoscope icon 107 (FIG. 2B) to re-establish the surgical image data as previously discussed. These are provided as just some examples of the different configurations that could be used achieving the same results of single input selection for quick routing of image data.

Figure 5:
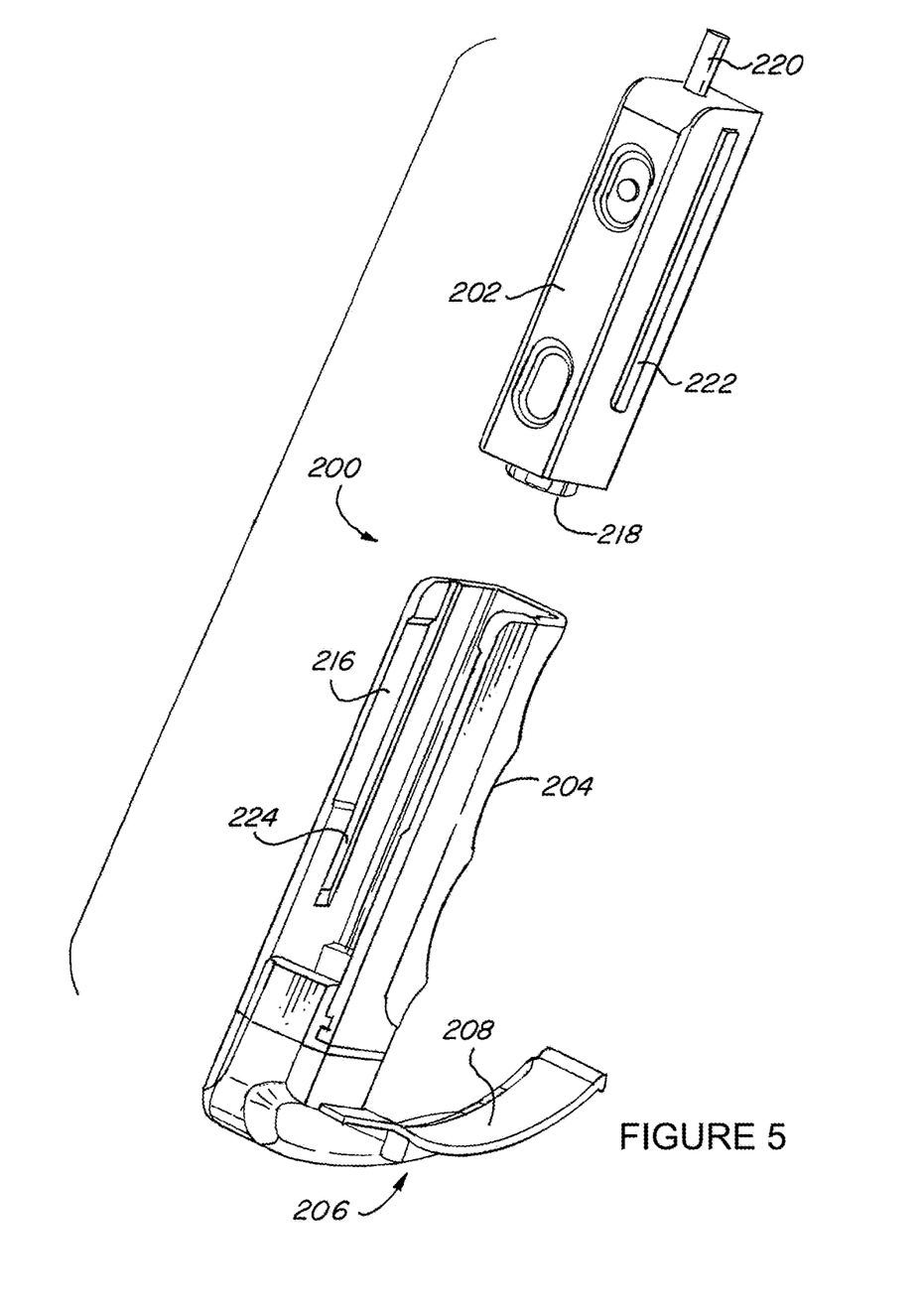
FIG. 5 is an illustration of a video laryngoscope according to an embodiment of the present invention of FIG. 1.
Figure 6:
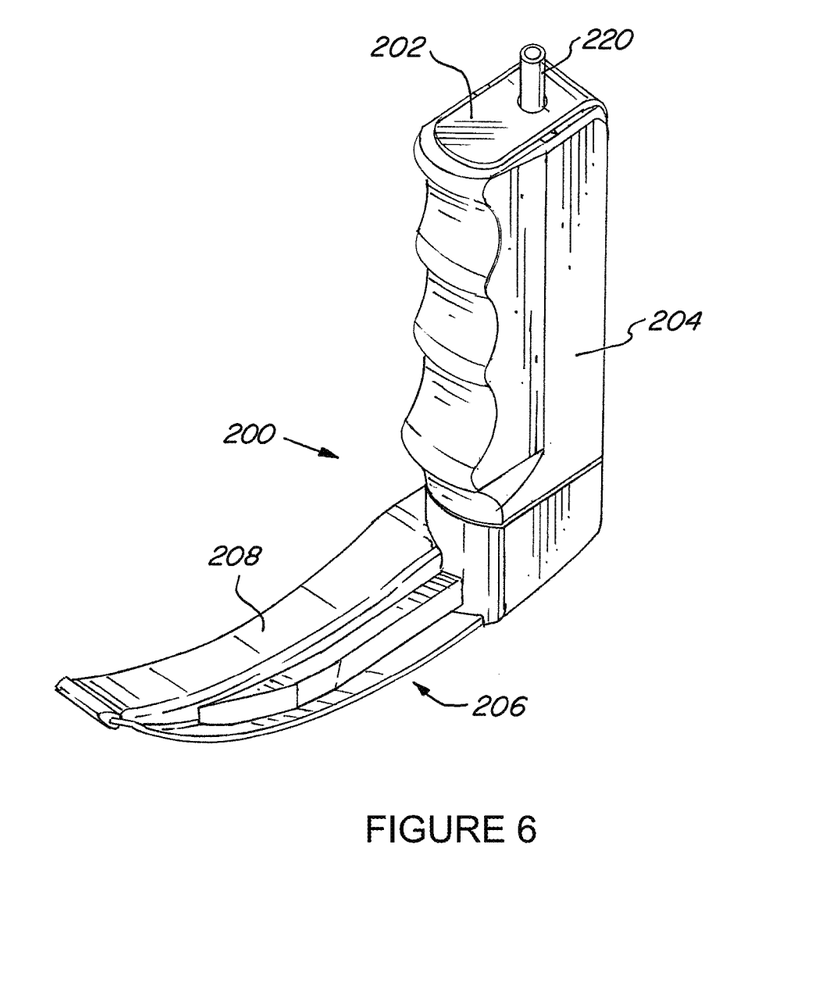
FIG. 6 is an illustration of a video laryngoscope according to an embodiment of the present invention of FIG. 1.
Figure 7:
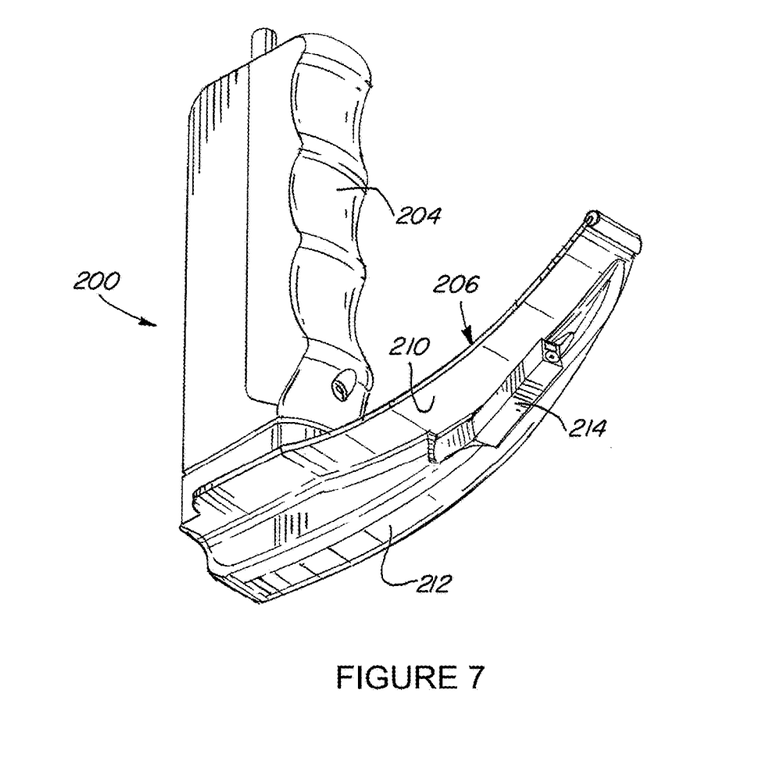
FIG. 7 is an illustration of a video laryngoscope according to an embodiment of the present invention of FIG. 1.

FIGS. 5-7 illustrate one particular embodiment of video laryngoscope 200. For example, video laryngoscope 200 may comprise a camera 202 that may be detachably connected to a handle 204 of the video laryngoscope. The handle 204 includes a blade 206 having, in this embodiment, a curved upper surface 208 and a curved lower surface 210. Also shown in FIGS. 5-7 is a bottom surface 212 within which the image channel(s) reside transmitting laryngoscope image data to camera 202. An imager 214 is provided on the underside of the blade 206.

The handle 204 is provided with a cavity 216 within which the camera 202 may be inserted and securely held. A camera connector 218 is located on one end of camera 202 and is designed to engaged with a handle connector (not shown) positioned in the bottom of cavity 216.

The camera 202 is provided with a protrusion 222, which may be in the form of a raised ridge on the exterior surface of camera 202 that is designed to engage with a recess 224 provided on an inner surface of cavity 216. In this manner, the camera 202 may be slid into cavity 216 such that the connectors engage (there may be an audible "click" when fully inserted) and the engagement of the protrusion 222 with the recess 224 maintains the camera 202 securely in cavity 216.

A connection 220 is provided at a top end of camera 202 for the transmission of laryngoscope image data. It should be understood however, that even though a portion of a cable (connection 220) is illustrated, a wireless configuration is contemplated that could provide for wireless transmission of the laryngoscope image data to the system for display on the various selected display(s).

While the invention has been specifically described in connection with certain specific embodiments thereof, it is to be understood that this is by way of illustration and not of limitation and that various changes and modifications in form and details may be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. An operating room control system comprising:
 a computer having a network connection and a storage accessible by said computer;
 an imaging device generating surgical image data;
 an interface including a touchscreen;
 a video laryngoscope generating laryngoscope image data;
 a controller adapted to route image data from the imaging device and the video laryngoscope to a plurality of destinations, the controller coupled to said computer and connected to:
  said imaging device;
  said interface; and
  said video laryngoscope;
 the touchscreen adapted to control routing of image data from the imaging device and the video laryngoscope to the plurality of destinations;
 the plurality of destinations including a first display and a second display coupled to said controller where said surgical image data is routed to and presented on said first and second displays based at least in part on programmed settings;
 in response to a single selection of the interface, routing of the surgical image data to said first and second displays is immediately interrupted and said laryngoscope image data is automatically routed to said first and second displays based at least in part on the programmed settings.

2. The operating room control system of claim 1 wherein the laryngoscope image data shown on said first display is automatically routed to and saved on said storage.

3. The operating room control system of claim 1 wherein in response to a single selection of the interface a second time, routing of the laryngoscope image data to said first and second displays is immediately interrupted and routing of surgical image data to said first and second displays is reestablished.

4. The operating room control system of claim 3 wherein routing of surgical image data to said first display further includes routing of surgical image data to said storage, and upon reestablishment of the routing of surgical image data to said first display, routing of surgical image data to said storage is also reestablished.

5. The operating room control system of claim 1 wherein the single selection of the interface comprises an icon on said touchscreen.

6. The operating room control system of claim 5 wherein upon the single selection of said interface, the laryngoscope image data is automatically displayed on said touchscreen.

7. The operating room control system of claim 1 further comprising a voice control system coupled to said controller and the single selection of the interface comprises a voice command detected by the voice control system.

8. The operating room control system of claim 1 further comprising a gesture recognition control system coupled to said controller and the single selection of the interface comprises a gesture recognized by the gesture recognition control system.

9. The operating room control system of claim 1 further comprising at least one medical tool coupled to said controller, wherein upon the single selection of the interface, the functioning of said at least one medical tool is automatically changed.

10. The operating room control system of claim 9 wherein the function change of said at least one medical tool is to set the medical tool to a predetermined setting.

11. The operating room control system of claim 9 wherein said at least one medical tool is selected from the group consisting of: catheterization devices, bi-polar cutting devices, lasers, rotating cutting devices, cell collection devices, suction devices and combinations thereof.

12. The operating room control system of claim 9 further comprising at least one piece of medical equipment coupled to said controller, wherein upon the single selection of the interface, the functioning of said at least one piece of medical equipment is automatically changed.

13. The operating room control system of claim 12 wherein the function change of said at least one piece of medical equipment is to set the at least one piece of medical equipment to a predetermined setting.

14. The operating room control system of claim 12 wherein said at least one piece of medical equipment is selected from the group consisting of: insufflation equipment, irrigation equipment, vacuum equipment, respiratory equipment and combinations thereof.

15. The operating room control system of claim 1, wherein said touchscreen comprises said first or second display.

16. An operating room control system comprising:
a computer having a network connection;
a storage accessible by said computer;
a touchscreen having an interface;
an imaging device generating surgical image data;
a video laryngoscope generating laryngoscope image data;
a controller coupled to said computer and said touchscreen, said controller connected to:
the imaging device;
the video laryngoscope;
at least one medical tool;
at least two displays coupled to said controller where image data is routed to and presented on said at least two displays based at least in part on programmed settings;
upon a single selection of the interface, routing of the surgical image data to said at least two displays is immediately interrupted and the laryngoscope image data is automatically routed to said at least two displays based at least in part on the programmed settings.

17. The operating room control system of claim 16 wherein the laryngoscope image data shown on said at least two displays is automatically routed to and saved on said storage.

18. The operating room control system of claim 16 wherein said interface comprises an icon on said touchscreen.

19. The operating room control system of claim 16 wherein said at least one medical tool is selected from the group consisting of: catheterization devices, bi-polar cutting devices, lasers, rotating cutting devices, cell collection devices, suction devices and combinations thereof.

20. The operating room control system of claim 16 wherein upon the single selection of the interface, the functioning of said at least one medical tool is automatically changed.

21. The operating room control system of claim 20 wherein the function change of said at least one medical tool is to set the medical tool to a predetermined setting.

22. The operating room control system of claim 16 further comprising at least one piece of medical equipment coupled to said controller, wherein upon the single selection of the interface, the functioning of said at least one piece of medical equipment is automatically changed.

23. The operating room control system of claim 22 wherein the function change of said at least one piece of medical equipment is to set the at least one piece of medical equipment to a predetermined setting.

24. The operating room control system of claim 22 wherein said at least one piece of medical equipment is selected from the group consisting of: insufflation equipment, irrigation equipment, vacuum equipment, respiratory equipment and combinations thereof.

* * * * *